(12) United States Patent
Mittelstädt et al.

(10) Patent No.: US 10,350,034 B2
(45) Date of Patent: Jul. 16, 2019

(54) BENDABLE PROSTHESIS POST AND ANGULAR ADJUSTMENT METHOD

(71) Applicant: DENTSCARE LTDA, Joinville—Santa Catarina (BR)

(72) Inventors: Friedrich Georg Mittelstädt, Joinville-Santa Catarina (BR); Adalberto Lippmann, Joinville-Santa Catarina (BR); Bruno Lippmann, Joinville-Santa Catarina (BR); Inco Hinz, Joinville-Santa Catarina (BR); Pedro Américo Aguilera, Joinville-Santa Catarina (BR); William De Souza Wiggers, Joinville-Santa Catarina (BR)

(73) Assignee: DENTSCARE LTDA, Joinville (BR)

( * ) Notice: Subject to any disclaimer, the term of this patent is extended or adjusted under 35 U.S.C. 154(b) by 247 days.

(21) Appl. No.: 14/408,228

(22) PCT Filed: Jun. 13, 2013

(86) PCT No.: PCT/BR2013/000209
§ 371 (c)(1),
(2) Date: Dec. 15, 2014

(87) PCT Pub. No.: WO2013/188939
PCT Pub. Date: Dec. 27, 2013

(65) Prior Publication Data
US 2015/0173863 A1    Jun. 25, 2015

(30) Foreign Application Priority Data

Jun. 18, 2012 (WO) ................. PCT/BR2012/000187

(51) Int. Cl.
*A61C 8/00* (2006.01)
*A61C 13/34* (2006.01)
*A61C 19/04* (2006.01)

(52) U.S. Cl.
CPC .......... *A61C 8/0053* (2013.01); *A61C 8/0069* (2013.01); *A61C 13/34* (2013.01); *A61C 19/04* (2013.01)

(58) Field of Classification Search
CPC .................................................... A61C 8/0053
(Continued)

(56) References Cited

U.S. PATENT DOCUMENTS 3,562,912 A    2/1971   Edelman
4,109,383 A    8/1978   Reed et al.
(Continued)

FOREIGN PATENT DOCUMENTS

DE    29817955       12/1998
EP    2438885 A1 *   4/2012   ........... A61C 8/0051
(Continued)

*Primary Examiner* — Wade Miles
*Assistant Examiner* — Matthew P Saunders
(74) *Attorney, Agent, or Firm* — Hogan Lovells US LLP (57) ABSTRACT

A BENDABLE PROSTHETIC ABUTMENT includes a guiding and anchoring segment, a connection zone, for connecting to an implant arranged on a gingival tissue for receiving a prosthetic abutment model, an intermediate restriction for angular orientation, a mounting and fastening portion forming an upper portion of the bendable prosthetic abutment for receiving a prosthesis, and a sacrificial and anchoring zone which has a diameter greater than a diameter of the connection zone so as to define a protuberant ring-shaped shoulder arranged between the intermediate restriction (4) and the connection zone (2) for connecting to an implant and anchoring in a cavity.

11 Claims, 6 Drawing Sheets

(58) Field of Classification Search
USPC .......................................................... 433/173
See application file for complete search history.

(56) References Cited

U.S. PATENT DOCUMENTS

| | | | |
|---|---|---|---|
| 4,187,609 A | | 2/1980 | Edelman |
| 4,217,100 A | | 8/1980 | Edelman |
| 4,253,833 A | | 3/1981 | Edelman |
| 4,276,026 A | | 6/1981 | Edelman |
| 4,645,453 A | * | 2/1987 | Niznick ............... A61C 8/0018 433/173 |
| 4,758,161 A | * | 7/1988 | Niznick ............... A61C 8/0053 433/173 |
| 4,768,956 A | | 9/1988 | Kurpis |
| 4,799,886 A | * | 1/1989 | Wimmer ............... A61C 8/0019 433/176 |
| RE33,796 E | * | 1/1992 | Niznick ............... A61C 8/0001 433/173 |
| 5,695,334 A | | 12/1997 | Blacklock et al. |
| 5,842,859 A | | 12/1998 | Palacci |
| 6,945,779 B2 | | 9/2005 | Richmond |
| 2003/0003419 A1 | * | 1/2003 | Ihde ....................... A61C 8/001 433/176 |
| 2007/0264613 A1 | * | 11/2007 | Ihde ....................... A61C 8/001 433/176 |
| 2011/0097689 A1 | | 4/2011 | Thome |
| 2014/0170597 A1 | * | 6/2014 | Honig .................. A61C 8/0053 433/173 |

FOREIGN PATENT DOCUMENTS

| | | |
|---|---|---|
| WO | 2000002495 | 1/2000 |
| WO | 2005074832 | 8/2005 |
| WO | 2015011312 | 1/2015 |

* cited by examiner

BENDABLE PROSTHESIS POST AND ANGULAR ADJUSTMENT METHOD

The present invention relates to a definitive and bendable prosthetic abutment and to the corresponding angular adjustment method, the method being in particular characterized by a customized mechanical forming process that helps dental surgeons and/or dental prosthesis technologists to orient the exposed part of the abutment with an inclination angle that makes it easier to mount the future prosthetic crown by following functional and aesthetic criteria without compromising the dimensional and mechanical properties of a definitive and bendable prosthetic abutment, pertaining to field of dental implantology

BACKGROUND

Nowadays there are different ways to restore absent teeth, consisting of removable or fixed prosthetic solutions, according to the possibility of each case. Natural teeth can be restored through total or partial removable prosthesis or unitary or multiple fixed prosthesis above natural teeth or implants. The dental implant is a device that simulates a dental root and it has the objective of restoring the dental crown through an abutment—also known as pillar or connector—which is connected to an osseointegrated dental implant and supports the prosthetic crown which will assume the aesthetics and function of a tooth.

The connection of the abutment to the implant is usually made by screwing or through a system of frictional fitting known as Morse taper, the later showing better sealing results between the implant and the abutment, besides having self-fixation properties as the masticatory force contributes to the better interlock of the parts. One way of connection is carried out by screwing through a central portion in the abutment, which receives a proper screw threaded inside the implant. This method of fixation is still very much used, although it presents problems of fatigue fixing, which promotes loosening of the screw, necessitating maintenance of the prosthesis.

In the phases of implant installation, there are some previous treatments/maneuvers to be executed on the receiving bone bed. Firstly, the space readiness and quality of the receiving place of the implant is checked and if necessary, the use of bone grafts to make the implant installation possible can be considered. This phase of installation of implants is identical for all of the types of dental prosthesis and the technique, as well as the processes, is well known now.

The bone tissue receives hole operations with special drills specifically gaged for adaptation of the chosen implant, considering its height and diameter. Still in this surgical act, the implant is threaded to the bone through a specific key until reaching the appropriate insert level, when then the implant receives a coupled or screwed cover right before the gum tissue is sutured, covering the implant completely. Starting from this moment, the inertia of the system promotes the phenomenon known as osseointegration that consists of the formation of a stable and functional union between the bone and the surface of the implant, what usually happens in a period from 3 to 6 months.

Once the implant is osseointegrated, the beginning of the prosthetic sequence is given. Surgical access to the implant is done through a small gum incision, and then the protecting cover of the implant is removed and replaced by a healing abutment, which remains in the place for about 2 weeks and has the objective of shaping the gum for subsequent adaptation of a prosthetic abutment. This abutment consists of the link that joins the dental crown to the implant, in other words, it is the communication between the tooth and the artificial root.

A diversity of abutments exists with different indications that vary according to the case, respecting factors such as the prosthesis type (fixed or removable) that is wanted, how many implants that will be used in the prosthesis (isolated or multiple elements), area of the tooth to be replaced (anterior or posterior), if the abutment will have to be customized, character of the prosthesis (temporary or definitive), gingival morphology (thick or thin) and if it is necessary to compensate some inclination of the implant, etc.

Among the existing problems found in the installation of implants, we can mention the lack of enough bone and with good enough quality in the area to receive the implant. Another limiting situation is the morphology of the existing bone itself. There are some ways to overpass the mentioned issues by using bone graft, shorter implants or, most commonly, placing implants in an angled way in order to find adequate bone support. That will make it necessary to use angled abutments, that is, abutments connecting to the implant that are angled to compensate the non-ideal implant axis.

The presence of acquired or congenital bone deformities should be considered in the preparatory surgeries in order to reestablish the anatomy and the morphology of the bone and, consequently, of the gum tissue that recovers it, aiming for the best aesthetic result in the adaptation of the prosthesis.

In general, in order to allow several adaptations of the prosthesis according to the biomechanical needs of each patient, angled prosthetic abutments with predefined angles are used, the angles ranging from 0° and 25° or 30°, which are molded or machined.

Although quite useful and sometimes indispensable, existing angled abutments have some limitations, the main one being the fact that they cannot provide intermediate or customized inclinations and also the fact that most manufacturers offer only one or two alternative angulations. This limitation makes it difficult for the professional to achieve perfect compensation in angles for all cases, since the desired compensation may not be the one offered by the market.

Another drawback of those pre-angled abutments is related to the need of inventories in the clinic to assist the diversity of clinical cases, otherwise the professional will be subject to one period of delivery of the special components.

Among other existing concepts to facilitate angled abutments are included the embedded, machined or molded components such as those shown in the patent documents PI9604737-2 and WO2010150188. In these cases when there is the need for assembling the components, it is obvious that the more components to the same physical space, the less space is available for walls and heights to dispose each part of the set, showing the possible structural weaknesses of those systems.

We can also mention the patent document US2011275030 that introduces a slopping abutment of single body and Morse taper that solves several problems as compared to the previous state of the art. Said document presents a schematic view partly in section of an area of the jaw containing angled abutments (see FIG. 6), where one can observe the method of positioning of the abutments for aesthetic alignment.

Despite the constant evolution, in all of the cases above it can be observed that the prior art only presents abutments built with preconceived angles, as in the case of patent US2011275030 typically in groups of 10, 15, 20, and 30 degrees, and not from degree to degree, for instance, creating mismatches and forcing the professional to acquire a stock of components to suit each clinical case, or then await order periods for each specific component used in each customer as these are products of high precise construction.

An alternative for determining the appropriate angle is disclosed in patent document U.S. Pat. No. 4,758,161, which introduces a thermoplastic coping insert for shaping models to be used to achieve definitive prosthetic abutments.

Referred coping insert comprises a lower portion that fits into an opening in an osseointegrated implant; an abutment head joined to the top surface of the dental implant; a bendable restriction or groove to facilitate bending of the insert at the restriction when the insert is heated to the softening temperature of a thermoplastic for determining the angle according to the biomechanical needs of each patient, such angle being determined at the mouth, that is, at the site of the implant; and a mounting area atop the restriction for receiving and supporting a dental prosthesis.

Initially, the insert is heated in order to be molded to the proper inclination, and then it is positioned in the mouth and later removed and used as a temporary template to shape a model for achieving a definitive prosthetic abutment.

Thus, the professional achieves the definitive prosthetic abutment with the ideal inclination for each patient, the definitive prosthetic abutment being shaped by any convenient material such as gold.

Another alternative to angular orientation of the prosthesis is disclosed in the patent document U.S. Pat. No. 4,645,453, which reveals a bendable adapter provided with a means of connecting to an implant positioned in the gum tissue; an intermediate narrow portion that is necked down to provide a flexible region close to the gum tissue; and, at the upper end, a mounting and fastening area for a prosthesis. Thus the projecting part of the bendable adapter may take various forms to maximize aesthetic requirements of the patients.

Figure 1:
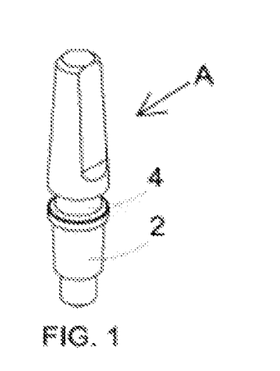
FIG. 1 illustrates a perspective view of a model of cemented, definitive and bendable prosthetic abutment (A), in a particular embodiment, comprising a conical connection region (2)

Disadvantageously, this patent document presents an intermediate narrow portion that is necked down to provide a flexible region close to the gum tissue, as shown in FIG. 1, reference 26, comprised of two sections at an angle converging on a straight section, which may cause cracks in the regions of convergence between the compressed angled and straight sections. These cracks may cause fatigue cracking with a few charging cycles.

Moreover, both alternatives disclosing prosthetic abutments provided with narrow regions for angular orientation do not define a customized bending method for definitive prosthetic abutments to help dental surgeons and/or prosthetic technologists to determine an inclination angle to each patient, in an individualized and accurate manner, without compromising the dimensional and mechanical properties of the abutment.

Solution and Advantages

Notwithstanding the alternatives in the state of the art related to implant systems, in particular bendable prosthetic abutments, the applicant, through research and technical tests, has observed that the implant system could be improved based on the previously described drawbacks of the existing techniques.

Thus, it was possible to develop a new concept of implant comprising an angular adjustment method of a definitive bendable prosthetic abutment having a new constructive form and designed to be mechanically shaped by means of a bending device involving a protection component of the exposed part of the abutment, for mounting of the prosthesis, such as a cover, and a component for determining the angle, such as a template for reference.

It should be noted that prosthetic abutments are pieces connecting the implant to the future prosthesis and are divided into two categories according to the type of prosthesis to be installed in the prosthetic phase, which can be cemented or screwed. Both cemented and screwed abutments have different heights to accommodate the gums and are segmented into bendable and non-bendable. The present patent document will consider the bendable versions only, which allow angular adjustment.

The purpose of the cemented bendable prosthetic abutment is to anchor the prosthesis through the cementation process in its superstructure, showing specific characteristics, and it can be bended in a conveniently positioned restriction.

The screwed bendable prosthetic abutment allows anchoring the future prosthetic crown by means of screws in the coronal portion which shows different diameter and height and also a threaded hole for connecting the prosthesis.

It is known that to provide adaptations that assist the needs for correcting angulations derived from implants placed at an angle, due to physiological limitations inherent to jawbones and jaws, it is essential that the prosthetic components provide a profile that is technically appropriate for each case.

Aiming to solve the above mentioned problems, the present invention proposes a definitive and bendable prosthetic abutment including the customized angular adjustment method to orient the exposed part of the abutment with an inclination angle that makes it easier to mount the future prosthetic crown, according to functional and aesthetic criteria without compromising the dimensional and mechanical properties of the bendable prosthetic abutment.

In a particular embodiment, the bendable prosthetic abutment shows a single body comprising a guiding and anchoring segment, followed by a connection with an osseointegrated implant (not depicted); a sacrificial and anchoring zone minimally larger than the external geometry of the zone for connection, followed by a restriction in the lower third to achieve angular adaptation; and adjoining the latter, a mounting and fastening portion for a screwed or cemented prosthesis.

Preferably, the zone for connection is conical shaped consistent with a cavity arranged within the implant so as to promote fastening by means of a system of frictional fitting known as Morse taper.

Considering the possibility of different gingival heights, both models of prosthetic abutments, cemented or screwed abutments, may comprise a variation in height for compensation, particularly in the restriction, which may vary according to a relationship between the smallest height and diameter of the restriction.

In one embodiment, the screwed abutment model may further comprise a conical portion from the restriction with a consistent and convenient geometry so as to allow adaptation of gingival tissue during its regeneration.

Preferred method of angular adjustment comprises a customized mechanical forming process involving a bending device; a reference abutment made of easily bendable plastics, and having a geometrical shape similar to that of a definitive prosthetic abutment; a protective cover to be coupled to the mounting portion of a definitive prosthetic abutment for a prosthesis; and a sacrificial and anchoring zone associated with the definitive prosthetic abutment, said sacrificial zone having been mentioned before, and which is used to anchor the definitive prosthetic abutment to the bending device.

For a better understanding of the embodiments of the invention, it will be understood that the models of bendable prosthetic abutments refer to definitive prosthetic abutments which are conveniently connected to permanent implants, aiming to differentiate the reference abutment, made of easily bendable plastics, to determine the proper angulation for said definitive prosthetic abutment.

Said method of angular adjustment of a definitive prosthetic abutment comprises the following steps: positioning and connection of a reference abutment, made of easily bendable plastics, in an internal cavity of an implant in the mouth; execution of the bend by the professional who determines the proper angle by manually warping the rod in the restriction, and by checking the occlusal condition of the patient; removal of the reference abutment from the implant cavity; placement and connection of the reference abutment to a cavity of the bending device; connection of a definitive prosthetic abutment model to the other cavity of the bending device, providing its anchoring through the sacrificial zone aligned with said reference abutment so as to allow comparison between the inclination of abutments; coupling of a protective cover to the mounting portion of the definitive prosthetic abutment; execution of the bend by gradual progress of an actuator directed to a cover coupled to the upper third portion of the definitive prosthetic abutment so as to warp the restriction until obtaining an equal angle between the reference abutment and the definitive prosthetic abutment; and pullout of the actuator, removing the angled abutment and its respective protective cover.

In one embodiment, a cemented prosthetic abutment, for example, may further comprise a second restriction in the mounting and fastening portion of prosthesis so as to allow further adjustments if needed, depending on the aesthetic and mechanical requirements of the implant system. Thus, another proper bending device may be used to bend the coronal portion of the prosthesis placement, which can comprise a suitable instrument to control the desired angle.

Through studies of morphology and structure, it was found that the warping causes dimensional changes in the regions close to the restriction and bending area, resulting in loss of roundness, flatness and cracks, making it difficult or even impossible the correct fitting of the abutment on the implant, precluding the use thereof. In order to avoid these deleterious effects to the abutment, said sacrificial and anchoring zone has been designed to act as a protection to the parts requiring dimensional accuracy while maintaining the original dimensional.

Another interesting and advantageous detail to be mentioned refers to the day-to-day logistics of the implantology professional, as through a simple set of tools for bending and using popularly known bending techniques, the same can perform all the dimensioning and tuning of the abutment in his laboratory by means of at least one bending angle setting in accordance with the clinical case of each patient, eliminating stocks or inventory orders and simplifying the process, without momentaneous reliance on external components or those with difficult quick implementation.

In order to better elucidate the embodiments of the invention, the schematic figures of a particular embodiment of the invention and its variants are shown, whose dimensions and proportions are not necessarily the actual ones, since the figures are only intended to introduce its various didactic aspects, whose scope of protection is determined only by the scope of the attached claims.

BRIEF DESCRIPTION OF THE DRAWINGS

The definitive and bendable prosthetic abutment and the corresponding angular adjustment method will be described below based on the accompanying drawings, in which.

DETAILED DESCRIPTION OF THE INVENTION

Figure 2:
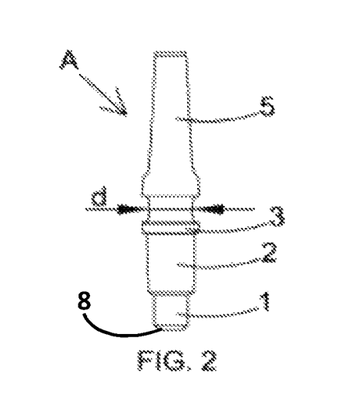
FIG. 2 illustrates a lateral view of the cemented, definitive and bendable abutment (A)

As illustrated in the attached drawings, the present invention relates to a new concept of a definitive and bendable prosthetic abutment including an angular adjustment method wherein:

FIGS. 1 and 2 illustrate a model of a cemented, definitive and bendable abutment (A), in a particular embodiment, which comprises a guiding and anchoring segment (1) followed by a zone (2) for connection to an osseointegrated implant (not depicted); a sacrificial and anchoring zone (3) minimally greater than the external geometry of the zone for connection (2); a restriction (4) in the lower third to achieve angular adjustment; and adjoining the latter a mounting and fastening portion of cemented or screwed prosthesis (5). In this particular embodiment, the prosthesis is anchored in the portion (5) through the cementing process.

Preferably, the zone for connection (2) is conical shaped concordant with a conical cavity arranged within the implant (not depicted) so as to promote fastening by means of a system of frictional fitting known as Morse taper.

Figure 2A:
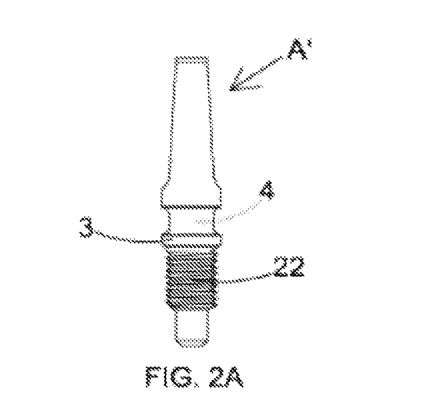
FIG. 2A illustrates a lateral view of a model of a cemented, definitive and bendable abutment (A) in a particular embodiment, comprising a threaded segment (22)

FIG. 2A illustrates a model of a cemented, definitive and bendable abutment (A) in a constructive variant comprising a screw threaded segment (22) as an example of another form of connection conveniently designed to be threaded into a cavity arranged within an implant (not depicted), so as to promote their connection and attachment.

However, the connection between the abutment and the implant can be carried out through any suitable means known in the art.

Figure 3:
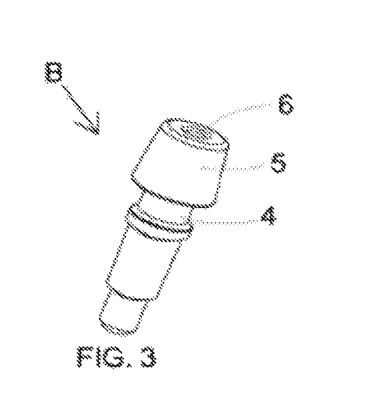
FIG. 3 illustrates a perspective view of another model of screwed, definitive and bendable abutment (B), in a particular embodiment, comprising a conical connection region (2)
Figure 4:
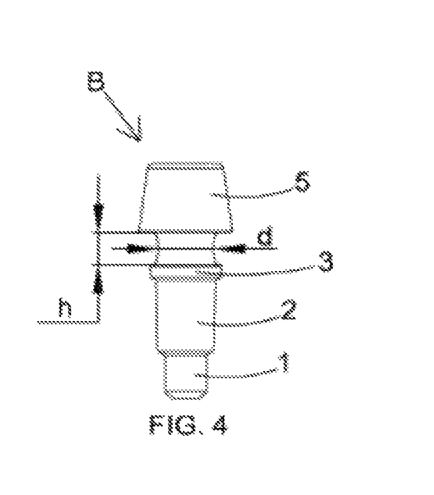
FIG. 4 illustrates a lateral view of the screwed, definitive and bendable abutment (B) with a possibility of variation in height (h) of the restriction (4) for compensation of different gingival heights.

FIGS. 3 and 4 illustrate another model of a screwed, definitive and bendable prosthetic abutment (B) comprising a mounting portion (5) with reduced area and provided with a threaded hole (6) for fastening of the prosthesis by means of a screw (not depicted), and keeping the other characteristics of said definitive prosthetic abutment model (A).

Being aware that, technically, the mechanical forming process in a bending operation may cause dimensional changes in the regions close to the bending point, said sacrificial and anchoring zone (3) has been designed having a larger metal volume in comparison with the zone for connection (2 or 22) to an osseointegrated implant (not depicted); said larger volume defining a ring-shaped shoulder with a larger diameter so as to provide an area to withstand all the efforts arising from the bending operation without compromising the requiring dimensional accuracy, especially in the zone for connection (2 or 22).

Any deformation in the zone (2 or 22) for connection to the implant may cause loss of roundness, flatness regions and cracks making it difficult or even impossible for the correct fitting of the abutment on the osseointegrated implant, for fastening through a system of frictional fitting known as Morse taper, screwing or similar.

Technically, the sacrificial and anchoring zone (3) promotes the anchoring of the abutment near the cavity (29 or 29') of the bending device (D), for execution of the bend. Because of the forces generated in the bending operation, the sacrificial zone (3) suffers intentional surface deformation as the anchoring region in the cavities (29 or 29') confers greater mechanical strength.

Advantageously, said sacrificial and anchoring zone (3) restricts the contact between the zone for connection (2 or 22) and the inner region of the cavity (29 or 29') to the bending device (D), which avoids any deformation of the dimensional and mechanical properties of this region, requiring dimensional accuracy to promote proper connection between the abutment and the implant.

The sacrificial and anchoring zone (3) is minimally larger than the external geometry of the zone for connection (2 or 22) so as to define a ring-shaped shoulder arranged between the bending area (4) and the zone for connection (2 or 22), the purpose of said ring-shaped shoulder being the anchoring of a definitive abutment in a cavity (29 or 29') of the bending device (D) so as to define a minimum distance between the zone for connection (2 or 22) and the cavities (29 or 29') arranged on a base (28) of the suitable bending device (D), which will be subsequently detailed.

Preferably, the sacrificial and anchoring zone (3) is substantially conical and has an angle ranging from 1 and 30° (degrees) to conveniently promote anchorage to withstand efforts arising from the bending operation of the definitive abutment. Moreover, said sacrificial and anchoring zone (3) is concordant with the internal geometry of cavities (29 or 29') so as to promote fastening through a concept known as Morse taper, as depicted in FIG. 17A, that will be subsequently detailed.

Additionally, any of the cavities (29 or 29') comprises a mounting area (12) arranged in the lower portion, concentrically and in low relief, in which the guiding and anchoring segment (1), including a tapered-tip region (8), of the definitive prosthetic abutment is connected so as to promote alignment, helping to anchor the abutment during the bending process in the restriction (4).

While segment (1) promotes proper guiding and anchoring in the mounting area (12), the ring-shaped shoulder (3) promotes anchoring of the abutment in the cavity (29 or 29') of the bending device (D) for the bending process.

Because of the forces generated in the bending operation and applied to the upper third portion (5) close to the restriction (4), the ring-shaped shoulder (3) suffers intentional surface deformation as the anchoring zone in the cavities (29 or 29') confers greater mechanical strength.

Preferably, the restriction (4) comprises a circular hyperboloid configuration, which defines an appropriate morphological structure to obtain a proper angle without compromising their mechanical strength necessary to withstand the occlusal forces generated during the act of mastication.

To achieve this goal, the restriction (4) is sized considering a relationship that must be obeyed, described in the ration between the height (h) by the smallest diameter (d) of the restriction (4), being at least 0.37, and it may increase according to the desired degree of inclination and the material used to manufacture the component.

The abutments may be made of materials compatible with the application, that is, commercially pure titanium and its alloys or stainless steel, and may have different metallurgical conditions, as for example, in the annealed state or in different degrees of cold deformation.

In one example of angular adjustment requiring an inclination of approximately 20 degrees, the smallest diameter (d) for the restriction (4) is approximately 2.25 mm, while the height (h) is approximately 1.5 mm, thus resulting in a ratio of approximately 0.67, that is, greater than 0.37.

Figure 5:
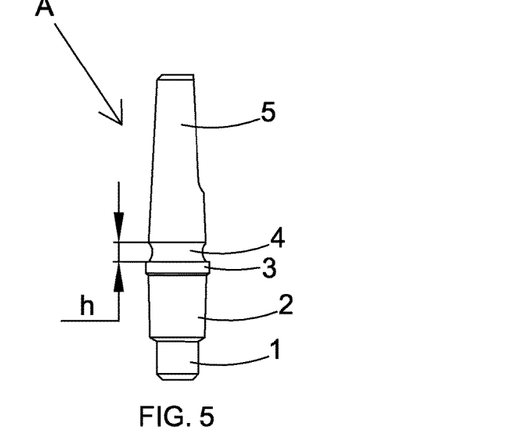
FIG. 5 illustrates a lateral view of a cemented, definitive and bendable abutment (A) in a constructive variant, showing an example of variation of height (h) of the restriction (4) for compensation of different gingival heights.

Considering the possibility of different gingival heights, both models of definitive prosthetic abutment (A and B) may comprise a variation in height (h) of the restriction (4) to compensate for different gingival heights, as depicted in FIG. 5.

FIG. 4 illustrates a model of a screwed, definitive and bendable prosthetic abutment (B) with a possibility of variation in height (h) of the restriction (4), while FIG. 5 illustrates a constructive variant for a cemented, definitive and bendable prosthetic abutment (A) showing a variation in height (h) of the restriction (4) for compensation of different gingival heights.

Figure 6:
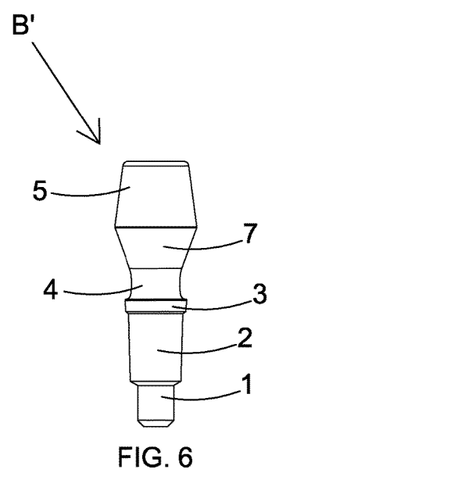
FIG. 6 illustrates a lateral view of a screwed, definitive and bendable abutment (B') in a constructive variant, further showing a conical portion (7) for compensation of different gingival heights.

FIG. 6 illustrates a screwed, definitive and bendable prosthetic abutment (B'), in one embodiment, additionally having a conical portion (7) for compensation of different gingival heights from the restriction (4) of concordant manner, and convenient geometry so as to allow the adaptation of gum tissue during regeneration.

Figure 7:
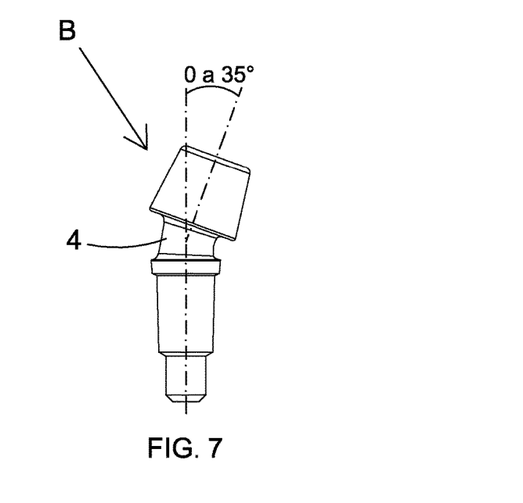
FIG. 7 illustrates a schematic view of a screwed, definitive and bendable abutment (B) showing an example of angular adjustment with the restriction (4) formed.

FIG. 7 illustrates a schematic view of a screwed bendable prosthetic abutment (B) showing an example of angular adjustment with an inclination ranging from 0 and 35 degrees.

Figure 8:
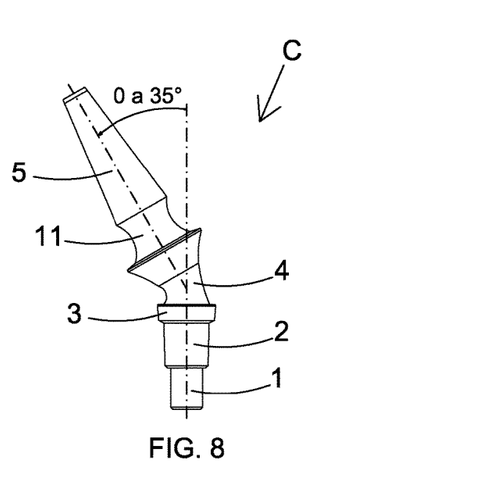
FIG. 8 illustrates a schematic lateral view of a cemented, definitive and bendable abutment (C) in a constructive variant, showing a restriction (4) in the lower third bent portion, and another restriction (11), optionally bendable, in the upper third portion (5) for settlement of the prosthesis.
Figure 9:
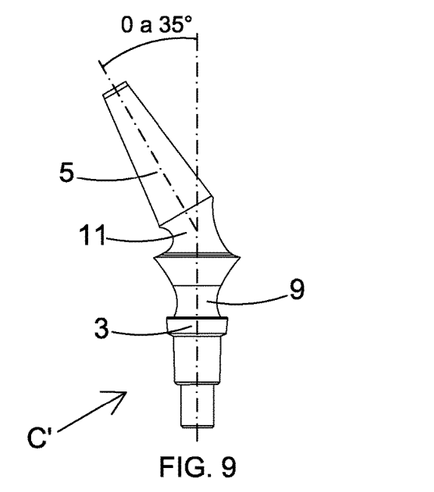
FIG. 9 illustrates a schematic lateral view of a cemented, definitive and bendable abutment (C') in a constructive variant, showing a restriction (11) in the upper third portion (5) for settlement of the bent prosthesis, and another restriction (9) bent in the lower third portion.
Figure 10:
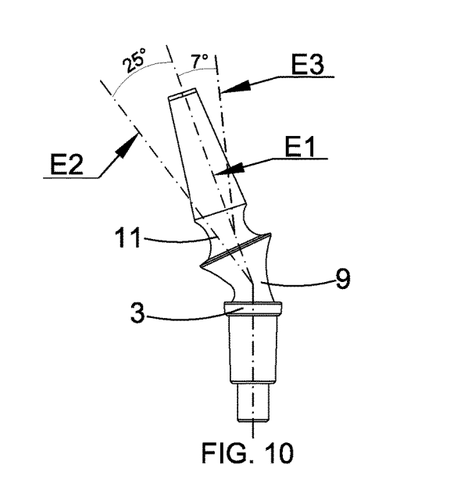
FIG. 10 illustrates a schematic lateral view of a simulation of bends of a cemented, definitive and bendable abutment, the restriction (9) in the lower third portion, in combination with the conformation of the restriction (11) in the upper third portion (5) for the mounting of the prosthesis allowing numerous adaptations of the prosthesis.

FIGS. 8, 9, and 10 show a constructive variant of a cemented prosthetic abutment (C and C') comprising a guiding and anchoring segment (1); followed by a zone (2) for connection to an osseointegrated implant (not depicted); a sacrificial and anchoring zone (3); a restriction (4 and 9) in the lower third to achieve angular adaptation; and, optionally, a second restriction (11) close to the mounting and fastening area for the prosthesis (5) in order to allow further adjustments if needed, depending on the aesthetic and mechanical requirements of the implant system. Thus, another suitable bending device may be used to promote bending of the mounting and fastening portion (5) before anchoring the prosthesis (not depicted).

One example of angular adjustment is shown in FIG. 8, in which the prosthetic abutment (C) was bent in the restriction (4) in the lower third with an inclination ranging from 0 and 35 degrees.

FIG. 9 shows another example of angular adjustment in which the definitive prosthetic abutment (C') was bent, alternatively, in the restriction (11) of the mounting and fastening portion (5) for the prosthesis (not depicted) with an inclination ranging from 0 and 35 degrees.

FIG. 10 shows, in illustrative manner, a summation of bends for a specific angular adaptation, which, based on the reference axis (E1), a bending carried out in the restriction (9) in the lower third can be observed with a suitable inclination of 25 degrees, represented by the axis (E2), and another restriction (11) of the mounting and fastening portion (5) for the prosthesis (not depicted), having a complementary inclination of 7 degrees, represented by axis (E3).

The preferred method of angular adjustment is formed by a customized mechanical forming process, preferably involving a proper bending device (D); a reference abutment (R), having a geometry similar to that of the bendable abutment models (A, A', B, B' or C), made of easily bendable plastics; a protective cover (31 or 32) to be conveniently coupled to the mounting portion (5) of a definitive prosthetic abutment (A, A', B, B' or C) for the prosthesis (not depicted); and said sacrificial and anchoring zone (3) associated with the abutment models previously described.

Figure 11:
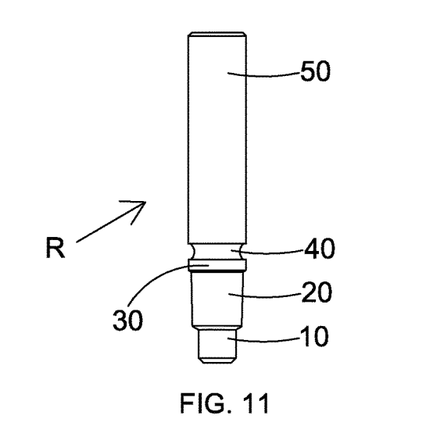
FIG. 11 illustrates a lateral view of a reference abutment (R), with a lower geometry similar to that of the already mentioned definitive prosthetic abutment models, differing primarily in an upper region formed by a reference rod (16)

FIG. 11 illustrates a reference abutment (R) made of easily bendable plastics, further comprising a guiding and anchoring segment (10); followed by a zone (20) for connection to an implant in the mouth; an anchoring region (30) minimally larger than the external geometry of the zone for connection (20); a restriction (40) in the lower third to achieve angular adjustment; and from this, a rod (50) for determining the appropriate angle.

Preferably, the anchoring region (30) of the reference abutment (R) is also substantially conical and has an external geometry consistent with the internal geometry of cavities (29 or 29') of the bending device (D) and the external cavity (not depicted) of an implant in the mouth (not depicted) so as to promote its connection to determine the angle by the professional in the mouth, and for reference in the bending operation of a definitive bendable prosthetic abutment (A, A', B, B' or C).

Said reference abutment (R) can be defined as a body of evidence, which allows the determination of an appropriate inclination by the professional, who simply places it in the mouth, the conical implant cavity (not depicted) promoting its connection by means of the anchoring region (3), and its cold conformation to obtain the desired angle by checking the patient's occlusal conditions.

Figure 12:
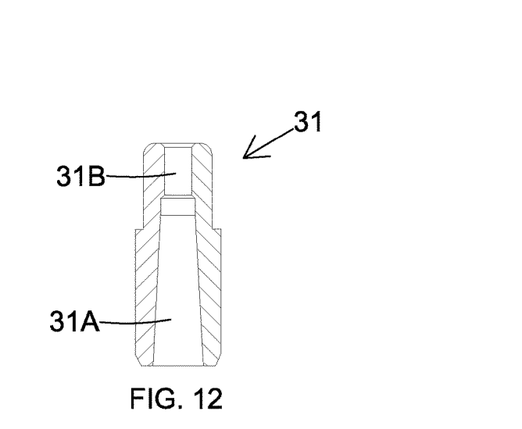
FIG. 12 shows a model of the protective cover (31) of the cemented, definitive and bendable abutments (A and C)

FIG. 12 shows a model of a protective cover (31) of a cemented definitive prosthetic abutment (A, A', or C), said cover (31) having a coupling region (31A) which is substantially conical in geometry and consistent with the external geometry of the coronal portion (5) so as to promote coupling into said coronal portion (5) of a cemented definitive prosthetic abutment; and also a through hole (31B) in its upper portion to make it easier to remove it after the warping process.

Figure 12A:
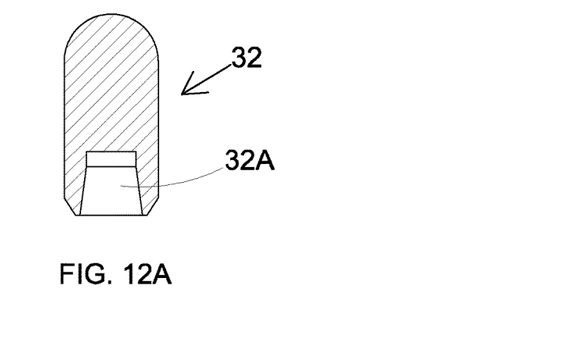
FIG. 12A shows a model of the protective cover (32) of the screwed, definitive and bendable abutments (B and B')

FIG. 12A shows another type of protective cover (32) of the upper third portion of the mounting and fastening portion (5) of a screwed definitive prosthetic abutment (B) for the prosthesis, said cover (32) having a coupling region (32A) which is substantially conical in geometry and consistent with the external geometry of the coronal portion (5) so as to promote coupling of the coronal portion (5) of a screwed definitive prosthetic abutment.

Technically, the protective cover (31 or 32), while protecting the upper third portion (5) against surface deformations, enables the distribution of loads in the regions close to the restriction (4), arising from the bending operation which, when coupled, allows a uniform angular orientation thus avoiding any deformation in the dimensional and mechanical properties of the upper third portion (5) of mounting and fastening for a prosthesis.

Figure 13:
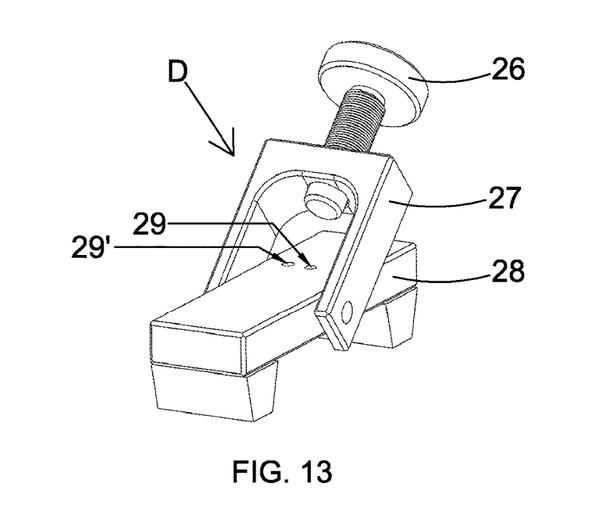
FIG. 13 shows a model of a bending device (D) for conformation of the definitive abutments.

FIG. 13 shows a model of appropriate bending device (D) comprising a base (28) which houses a cavity (29') for mounting a reference abutment (R), pre-bent, according to the ideal morphology of the patient's mouth, and another cavity (29) for mounting a definitive prosthetic abutment (A, A', B, B' or C) to be bent. Said bending device (D) further comprises a support (27) associated with an actuator (26), which will exert force through a warping displacement zone in contact with the protective cover (31 or 32) connected to a definitive abutment so as to bend thereof for angular adjustment.

Figure 14:
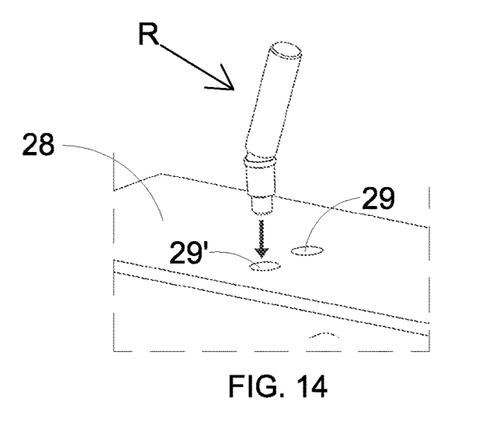
FIG. 14 shows a schematic view of the reference abutment (R) being connected in a cavity (29') of the bending device (D)

FIG. 14 shows a simulation of a step of positioning the reference abutment (R) in the cavity (29') arranged on the base (28) of the bending device (D), and in this step the reference abutment (R) comprises proper inclination determined by the professional in the mouth.

Figure 15:
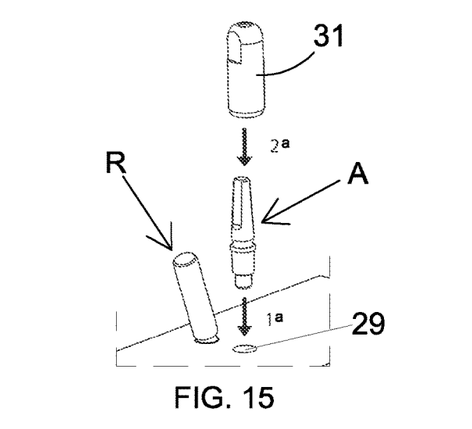
FIG. 15 shows a schematic view of a mounting sequence of the protective cover (31) in a definitive abutment model (A) with a bending device (D)

FIG. 15 shows a mounting sequence starting from the reference abutment (R) already anchored and with the appropriate inclination angle determined by the professional who, in the first step, positions and anchors the definitive bendable abutment model (A) in the cavity (29) arranged on the base (28) of the bending device (D) and subsequently makes the introduction and anchorage of said protective cover (31) in the mounting portion for the future prosthesis (5).

Figure 16:
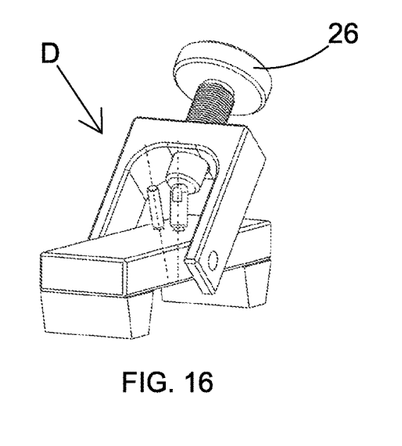
FIG. 16 shows a schematic view of the conveniently positioned and connected components in the cavities of the bending device (C)

FIG. 16 shows a sequence of completed preparation for the bending operation, in which through the rotary movement of the actuator (26), the bending of a definitive prosthetic abutment is started.

Figure 17:
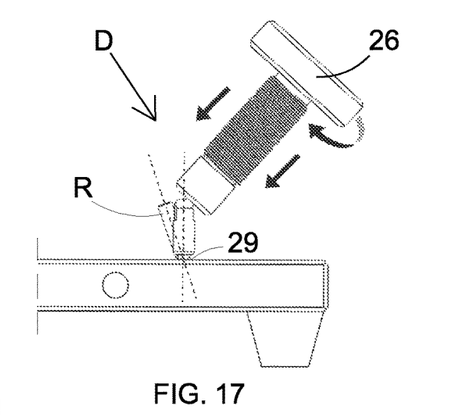
FIG. 17 shows a partial schematic sectional view simulating the progress of an actuator (26) associated with the bending device (D) for execution of the bend.
Figure 17A:
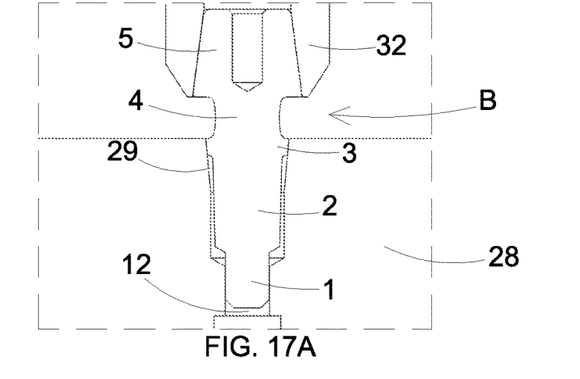
FIG. 17A shows a partial schematic sectional view of a definitive abutment model (B) connected to a cavity (29) of the bending device (D), comprising a protective cover (32) coupled to the mounting portion (5) for the prosthesis.

FIG. 17 shows a simulation of warping, where the gradual progress actuator (26) promotes the desired inclination until an equal angle is obtained between the reference abutment (R) and a definitive prosthetic abutment.

FIG. 17A illustrates a definitive prosthetic abutment model (B), properly anchored in a cavity (29) through the sacrificial zone (3) and connected concentrically to the mounting area (12) through the guiding and anchoring segment (1) arranged in the lower end of a definitive prosthetic abutment.

The guiding and anchoring segment (1) of the definitive prosthetic abutment (A, A', B, B' or C) and of the reference abutment (R) comprises an external geometry consistent with the internal geometry of the mounting area (12) arranged within the cavities (29 and 29') concentrically and in low relief, in order to promote the aligned connection of the abutments, definitive and reference abutments, and in the bending process of a definitive prosthetic abutment, said mounting area (12) helps anchoring for angular adjustment.

Figure 18:
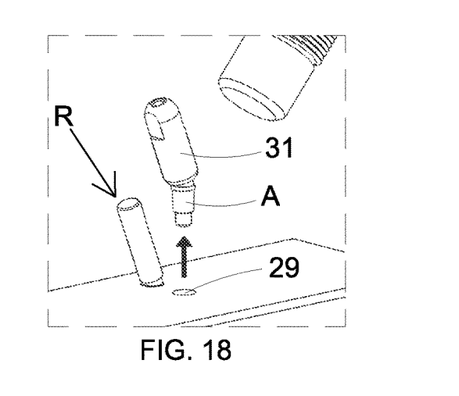
FIG. 18 shows a partial schematic view simulating the removal of a definitive abutment model (A) suitably angled in the bending device (D)

FIG. 18 shows the removal of the definitive prosthetic abutment (A) of the cavity (29) of the bending device (C) and subsequently the protective cover (31).

Figure 19:
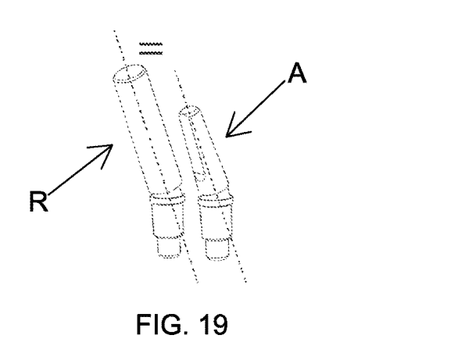
FIG. 19 shows a comparison between a definitive abutment (A) and a reference abutment (R) with similar angles.

FIG. 19 shows a comparison between a definitive prosthetic abutment model (A) and a reference abutment (R), bent at equal angles.

As previously mentioned in a particular embodiment, the present invention includes an angular adjustment method comprising the following steps:

a) placement and connection of the reference abutment (R) in the conical cavity of the implant in the mouth (not depicted) in order to promote its anchorage through the anchoring region (30);

b) execution of the bend by the professional who determines proper angle by manually flexing the rod (50) of the reference abutment (R) to promote warping of the restriction (4) by checking the patient's occlusal conditions;

c) removal of the reference abutment (R) of the cavity of the implant (not depicted);

d) placement and connection of the reference abutment (R) in the cavity (29') arranged on the base (28) of the bending device (D), promoting its anchoring through the anchoring region (3) and alignment through the guiding and anchoring segment (1) embedded in the mounting area (12) arranged within said cavity (29') concentrically and in low relief;

e) placement and connection of a definitive bendable prosthetic abutment (A, A', B, B' or C) in another cavity (29) of the bending device (D), promoting their anchorage through the sacrificial zone (3) and alignment through the guiding and anchoring segment (1) embedded in the mounting area (12), arranged within said cavity (29) concentrically and in low relief;

f) coupling of protective cover (31 or 32) in the mounting portion for the prosthesis (5);

g) execution of the bend by means of gradual progress of an actuator (26) directed towards the upper third portion (5) of a definitive prosthetic abutment model (A, A', B, B' or C) coated by a protective cover (31 or 32) so as to promote the bending of the restriction (4) to obtain equal angle between the reference abutment (R) and the definitive prosthetic abutment (A); and h) pullout of the actuator (26) and removal of the angled definitive abutment from the cavity (29) of the bending device (D), of respective protective cover (31 or 32), and the reference abutment (R) for angular adjustment.

Optionally, the reference prosthetic abutment (R) may be replaced by a device for determining the angle in the mouth, such as an intraoral goniometer which can be used in the mouth to determine the appropriate angle depending on the clinical need for each patient. This goniometer can be coupled onto the implant, inside the mouth, which will allow registration, via a pointer, the angle that best matches the alignment of the elements in the dental arch, considering the angle at which the implant was implanted.

In this condition, another suitable measuring instrument (not depicted), associated with the bending device may be used to control the angle measured in the mouth by the professional. The goniometer is an instrument known in the art, and used for checking angular measurements.

Figure 20:
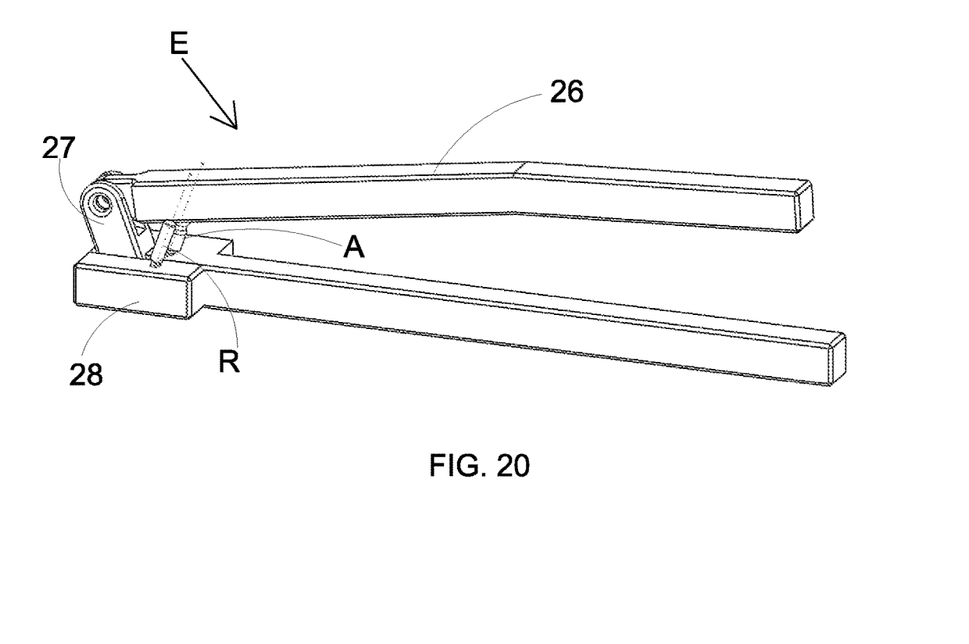
FIG. 20 shows an example of another type of bending device (E) in a schematic perspective view.

FIG. 20 shows as an example, another type of bending device (E) in schematic view, showing the abutments properly connected and angled, which can be used instead of the bending device (D), described as a particular embodiment, involving a proper angular adjustment method. Thus, other models can be used to achieve the same goal.

The bending device (E) also comprises a base (28) which houses a cavity (29') for mounting of a reference abutment (R) pre-bent, according to the ideal morphology of the patient's mouth, and another cavity (29) for mounting of a definitive prosthetic abutment (A, A', B, B' or C) to be bent. Said bending device (E) further comprises a support (27) associated with an actuator (26), which will exert force through a warping displacement zone, such as a lever, which, in contact with the protective cover (31 or 32) of a definitive abutment, promotes bending thereof for angular adjustment.

Variations and modifications with respect to the embodiments shown and described in the attached drawings will readily occur to a person skilled in the art without departing from the scope of the present invention as defined in the attached claims.

The invention claimed is:

1. A definitive bendable prosthetic abutment provided with a single body, the single body being a metal material, for bending to a definitive position at ambient temperature when positioned in a cavity (29) of a separate bending device (D), the prosthetic abutment comprising:

a guiding and anchoring segment (1), including a tapered-tip region, to promote alignment of the prosthetic abutment when positioned in the cavity (29) of the separate bending device (D);

a connection zone (2) connected to an end portion of the guiding and anchoring segment (1) and extending upwardly therefrom to connect to an implant when arranged on the gingival tissue, the connection zone (2) being conical shaped substantially similar to an internal geometry of a cavity arranged within the implant;

a sacrificial and anchoring zone (3) connected to an end portion of the connection zone (2) and having a diameter greater than a diameter of the connection zone (2) so as to define a bulbous-protuberant, ring-shaped shoulder to be positioned in the cavity (29) of the separate bending device (D) when being bent to the definitive position so that peripheral portions of the bulbous-protuberant, ring-shaped shoulder contact peripheral portions of the cavity (29) during the bending at ambient temperature and when positioned in the separate bending device (D), thereby to protect proximate portion of the prosthetic abutment requiring dimensional accuracy from deformation, the guiding and anchoring segment (1), the connection zone (2), and the sacrificial and anchoring zone (3) collectively defining a lower portion of the single body, the diameter of the sacrificial and anchoring zone (3) being greater than the diameter of the largest portion of the connection zone (2);

a bendable intermediate restriction (4) connected to the sacrificial and anchoring zone (3) and extending upwardly therefrom and positioned to define an intermediate portion of the single body to bend an upper portion of the single body at ambient temperature for angular orientation with respect to the lower portion for the definitive position when positioned in the cavity (29) of the bending device (D); and a mounting and fastening portion (5) connected to an end portion of the intermediate restriction and extending upwardly therefrom to receive a prosthesis to be mounted and fastened when positioned thereon, the mounting and fastening portion (5) defining the upper portion of the single body of the definitive bendable prosthetic abutment and being bendable at ambient temperature to an angular orientation with respect to the lower portion and about the intermediate restriction (4) when the lower portion is positioned in the cavity (29) of the bending device (D).

2. The definitive bendable prosthetic abutment according to claim 1, wherein the separate bendable device further includes a base (28) and the cavity (29) is positioned in the base (28), and wherein the sacrificial and anchoring zone (3) has a conical shape and has an external geometry shape consistent with an internal geometry shape of the cavity (29) of the base (28) of the separate bending device (D) when positioned therein, the sacrificial and anchoring device (3) defines a minimum distance between the connection zone (2) and the cavity (29) arranged on the base (28) of the separate bending device (D), thereby to promote anchoring of a definitive prosthetic abutment model for bending to the definitive position and to provide an area to withstand all the efforts arising from the bending operation.

3. The definitive bendable prosthetic abutment according to claim 2, wherein the sacrificial and anchoring zone (3) has an outer surface that extends outwardly from an outer surface of the end portion of the connection zone (2) at a preselected angle ranging from 1 and 30° (degrees), the sacrificial and anchoring zone (3) restricts the contact between the connection zone (2) and the cavity (29) to protect the connection zone (2) and to promote anchorage of the shoulder in the cavity (29) of the separate bending device (D) for bending the prosthetic abutment model to the definitive position.

4. The definitive bendable prosthetic abutment according to claim 1, wherein the intermediate restriction (4) is dimensioned based on a ratio between a height (h) of the intermediate restriction as defined by an extent between an upper end portion of the shoulder and the lower end portion of the mounting and fastening portion (5) and the smallest diameter (d) of the intermediate restriction (4), the ratio being at least 0.37.

5. The definitive bendable prosthetic abutment according to claim 4, wherein the height (h) of the intermediate restriction (4) comprises a preformed selected height in based on a preselected gingival tissue height of a mouth into which the abutment is to be positioned.

6. The definitive bendable prosthetic abutment according to claim 1, wherein the intermediate restriction (4) includes a conical portion (7) which has a height as defined by an extent between an upper end portion of the shoulder to the lower end portion of the mounting and fastening portions (5) and corresponds to a preselected gingival tissue height of a mouth into which the abutment is to be positioned, thereby to enable the adaptation of gum tissue during its regeneration.

7. The definitive bendable prosthetic abutment according to claim 1, wherein the guiding and anchoring segment (1) has an external geometry shape consistent with the internal geometry shape of a mounting area (12) arranged within the cavity (29) of the separate bending device (D) and to be arranged concentrically and in low relief therein, thereby to promote alignment and anchoring of a definitive prosthetic abutment for bending to the definitive position, and wherein the guiding and anchoring segment (1) has a smaller circumference than the connection zone (2).

8. The definitive bendable prosthetic abutment according to claim 1, wherein the intermediate restriction comprises a first restriction of the single body, and the definitive bendable prosthetic abutment further comprises a second restriction (11) of the single body positioned between and connected to the lower end portion of the mounting and fastening portion (5) and to an upper end portion of the intermediate restriction (4), the mounting and fastening portion (5) also having a bulbous-shaped lower portion thereof, and wherein the bendable intermediate restriction also has a circumferential profile which is arc-shaped concave.

9. The definitive bendable prosthetic abutment according to claim 1, wherein the single body comprises bendable material.

10. The definitive bendable prosthetic abutment according to claim 9, wherein shoulder of the sacrificial and anchoring zone (3) has a substantially bulbous-protuberant, ring-shape and deforms when the sacrificial and anchoring zone (3) is positioned in a cavity (29) of a separate bendable device (D) and during the bending to the definitive position.

11. The definitive bendable prosthetic abutment according to claim 10, wherein the connection zone (2) is externally threaded.

* * * * *